United States Patent [19]

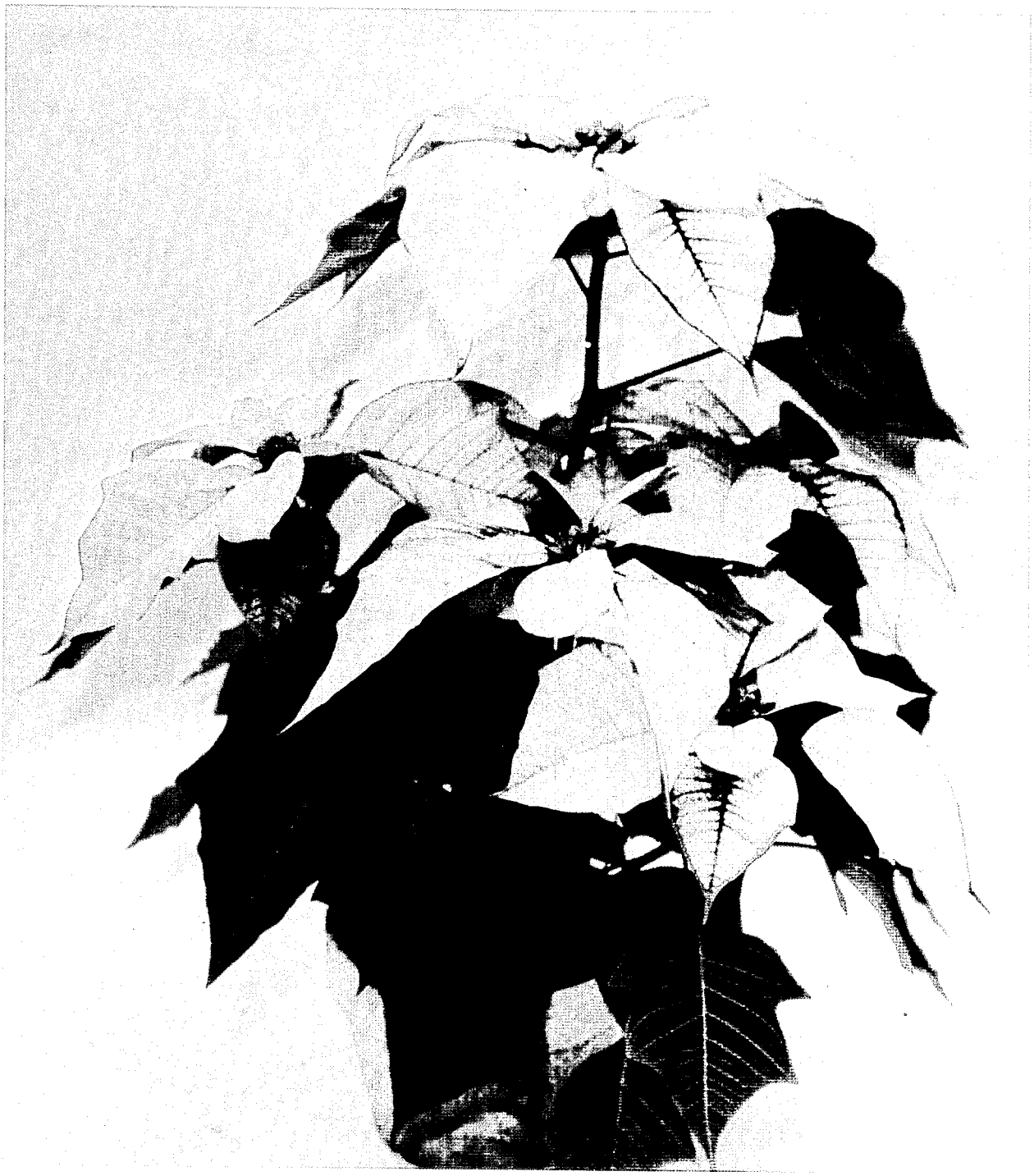

Hrebeniuk

[11] Plant 4,434

[45] Jul. 10, 1979

[54] POINSETTIA PLANT

[76] Inventor: Alexander Hrebeniuk, 7 Corner Rd., Perkasie, Pa. 18944

[21] Appl. No.: 893,758

[22] Filed: Apr. 5, 1978

[51] Int. Cl.[2] ..... A01H 5/00
[52] U.S. Cl. ..... Plt./86
[58] Field of Search ..... Plt./86

*Primary Examiner*—Robert E. Bagwill
*Assistant Examiner*—James R. Feyrer
*Attorney, Agent, or Firm*—Zachary T. Wobensmith, 2nd; Zachary T. Wobensmith, III

[57] ABSTRACT

A poinsettia plant is disclosed suitable for pot growth production which is free branching, with compact growth habits, hardy at relatively cool temperatures, has long bloom, has double flowers resistant to fading, has non-drooping foliage, retains its beauty and life at a temperature range of 50° F. to 60° F. and is a sport of Wonderstar, U.S. Plant Pat. No. 3,917.

1 Drawing Figure

1

This invention relates to marketable poinsettia plants of the species *Euphorbia pulcherrima.*

The present invention is for a new and distinct variety of poinsettia plant of the species *Euphorbia pulcherrima,* produced and originated by cross-breeding two different red seedlings with the definite goal of creating a new strong-growing and free-branching poinsettia plant variety which is hardy at relatively cool temperatures and is a sport from WonderStar, the subject of my U.S. Plant Pat. No. 3,917.

In selecting poinsettia plants for breeding, it was a primary object that the final result give the horticultural industry a new poinsettia plant which is commercially desirable. This new poinsettia plant is suitable for pot growth production that would branch freely, have a very compact habit that would obviate the need for chemical height control, be resistant to "dark spotting" when watered, and be resistant to fade with changes in temperature. A highly commercially advantageous feature of the invention is that the new poinsettia plant can be grown in relatively cool temperatures, preferably 58° F., but within a range of 50° F. to 60° F. When the plant has bloomed, its beauty and life can be held for about three months by maintaining the plant at a temperature of 50° F. All of these objects were achieved by this distinct new variety.

I have now produced and disclose herein a new, compact plant with desirable characteristics:

(1) A new plant that has the ability to produce 10 branches from a single pinched plant without chemical treatment, (2) A new poinsettia which can be initially raised at 58° F., which temperature can be lowered to 50° F. when half bloomed.

(3) A new poinsettia plant which can start blooming before Christmas, as early as the second week of November, and stay bloomed for three months, all without loose foliage or loose flowers.

(4) A new poinsettia plant which has double flowers which are resistant to fade.

(5) A new poinsettia plant which produces double flowers, as particularly contrasted with those poinsettia plants which yield single or triple flowers.

(6) A new poinsettia plant which can be watered without "dark spotting" resulting therefrom.

(7) A new poinsettia plant which has hardy foliage which is resistant to drooping.

2

(8) A new poinsettia plant which is self-branching.

(9) A new poinsettia plant from which more cuttings can be taken for rooting.

(10) A new poinsettia plant which has faster rooting cuttings.

(11) A new poinsettia plant which has pointed leaves.

(12) A new poinsettia plant which is resistant to bruising and thus better adapted for shipping.

(13) A new poinsettia plant which is more compact and has decreased tendency of the butts to separate.

(14) A new poinsettia plant in which the foliage and flowers retain their color for a longer period of time without fading, whether or not the plant is exposed to the sun.

(15) A new poinsettia plant which has greater resistance to root rot.

The accompanying photograph shows a typical specimen of my new variety with the colors being reproduced as closely as available photographic methods can define. The colors in this photograph and appended descriptive material are coded from Exotica Horticultural Color Guide, located at pages 37 and 38 of Exotica 3 Pictorial Cyclopedia of Exotic Plants (Century Edition) by Alfred Byrd Graf, published 1970 by Roehrs Company—Library of Congress Catalog Card No. 74-92881—except where common dictionary significance will be obvious. The Exotica Color Guide determinations, as stated at page 38, approximate Maerz and Paul "Dictionary of Color" and Royal Horticultural Society Colour Charts.

The description and photograph are taken from specimens asexually reproduced under my direction through natural growth at Perkasie, Pa., U.S.A.

Growth habit: Upright growth with medium height characteristics suitable for pot culture, obviating the need for chemical growth regulators. A distinctive growth characteristic of this plant is its ability to self-branch.

Rooting habit: Very fast. The roots develop within two weeks and are rot resistant.

Temperature: The new poinsettia plant can be grown in cool temperatures, as low as 50° F., preferably 58° F., yielding a hardy, beautiful plant. The highest desired growing temperature is 60° F. The plant can be maintained or held for three months at a 50° F. temperature.

Blooming season: The new poinsettia plant is a nine week variety, starting mostly in the second week of November.

Foliage: The leaves are spaced about the plant, 10 to 20 leaves or more, and are generally short and pointed, normally described as obovate in appearance (as described in Exotica). The leaf color on mature leaves is forest green (Code No. 77) on the upper side and meadow green (Code No. 76) on the underside. The ribs and veins are light. The edge is dark and smooth with single serrations. The underside is smooth.

Flowers (Cyathia): Each bract is generally pointed in shape, the upper side having a flat texture, and the underside having a smooth texture. The color on each side is blood-red (Code No. 27). Typically the number of bracts per stem range from 18 to 20. The length of a typical bract, in bloom, is 7 inches, with an overall width of 3 inches. The stamens and styles are blood-red (Code No. 27). The pollen and nectar cups are canary (Code No. 3). The new wood of this new variety is dark gray in color, which turns to dark green as the wood ages. The bark is smooth when new, and is rough when old.

I claim:

1. A new and distinct variety of poinsettia plant substantially as illustrated and described, characterized particularly as to novelty by its compact growth, self-branching habit, non-drooping foliage, and its ability to maintain its beauty and life at a temperature range of 50° F. to 60° F.

* * * * *

UNITED STATES PATENT AND TRADEMARK OFFICE

CERTIFICATE OF CORRECTION

PATENT NO. : Plant 4,434

DATED : July 10, 1979

INVENTOR(S) : Alexander Hrebeniuk

It is certified that error appears in the above-identified patent and that said Letters Patent is hereby corrected as shown below:

In column 1, paragraph 2 (lines 3-10) is revised to read as follows:

"The present invention is for a new and distinct variety of poinsettia plant of the species Euphorbia pulcherrima which is a sport of WonderStar, the subject of my U.S. Plant Patent No. 3,917. The sport was discovered by me in a cultivated area in Perkasie, Pennsylvania growing in a bed of plants of the parent cultivar WonderStar."

In column 1, paragraph 3 (lines 11-26) is revised to read as follows:

"This new poinsettia plant is suitable for pot growth production and branches freely, has a very compact habit that obviates the need for chemical height control, is resistant to "dark spotting" when watered, and is resistant to fade with changes in temperature. A highly commercially advantageous feature of the invention is that the new poinsettia plant can be grown in relatively cool temperatures, preferably 58°F., but within a range of 50°F. to 60°F. When the plant has bloomed, its beauty and life can be held for about three months by maintaining the plant at a temperature of 50°F."

UNITED STATES PATENT AND TRADEMARK OFFICE

CERTIFICATE OF CORRECTION

PATENT NO. : Plant 4,434

DATED : July 10, 1979

INVENTOR(S) : Alexander Hrebeniuk

It is certified that error appears in the above-identified patent and that said Letters Patent is hereby corrected as shown below:

In column 1, paragraph 4, the first line is revised to read as follows:

"Disclosed herein is a new,"

Signed and Sealed this

First Day of July 1986

[SEAL]

Attest:

DONALD J. QUIGG

Attesting Officer

Commissioner of Patents and Trademarks